(12) United States Patent
Shulock et al.

(10) Patent No.: US 12,303,396 B2
(45) Date of Patent: May 20, 2025

(54) ADJUSTABLE PATELLAR TENDON REALIGNMENT IMPLANT

(71) Applicant: ZKR ORTHOPEDICS, INC., Sausalito, CA (US)

(72) Inventors: Damien Shulock, San Francisco, CA (US); Jeffrey Halbrecht, San Francisco, CA (US); John Barrett, San Francisco, CA (US); Katherine J. Stephenson, Belmont, CA (US)

(73) Assignee: ZKR Orthopedics, Inc., Kentfield, CA (US)

( * ) Notice: Subject to any disclaimer, the term of this patent is extended or adjusted under 35 U.S.C. 154(b) by 652 days.

(21) Appl. No.: 17/316,233

(22) Filed: May 10, 2021

(65) Prior Publication Data

US 2021/0346165 A1   Nov. 11, 2021

Related U.S. Application Data

(60) Provisional application No. 63/022,977, filed on May 11, 2020.

(51) Int. Cl.
*A61F 2/38* (2006.01)
*A61F 2/46* (2006.01)
*A61F 2/30* (2006.01)

(52) U.S. Cl.
CPC ............ *A61F 2/3877* (2013.01); *A61F 2/461* (2013.01); *A61F 2002/30548* (2013.01);
(Continued)

(58) Field of Classification Search
CPC .... A61F 2/389; A61F 2/30734; A61F 2/3877; A61F 2/461; A61F 2002/30538;
(Continued)

(56) References Cited

U.S. PATENT DOCUMENTS

| 3,872,519 A | 3/1975 | Giannestras et al. |
| 3,879,767 A | 4/1975 | Stubstad |

(Continued)

FOREIGN PATENT DOCUMENTS

EP   2298179 A2   3/2011

OTHER PUBLICATIONS

Chow et al.; Fracture of the tibial tubercle in the adolescent; The Journal of Bone and Joint Surgery; 72(2); pp. 231-234; Mar. 1, 1990.
(Continued)

*Primary Examiner* — Sarah W Aleman
(74) *Attorney, Agent, or Firm* — Fredrikson & Byron, P.A.

(57) ABSTRACT

An orthopedic implant with an inferior portion having a tibia contact surface configured to extend over a tibia; a superior portion opposite to the inferior portion having a tendon contact surface configured to change a position of a patellar tendon by lifting or tilting the patellar tendon when the curved surface of the first portion is engaged with the tibia; a fixation mechanism adapted to attach the orthopedic implant to the tibia; and an adjustment mechanism adapted to change a distance between the tendon contact surface and the tibia contact surface. The invention also includes a method for repositioning a patellar tendon of a patient.

11 Claims, 5 Drawing Sheets

(52) U.S. Cl.
CPC ............... *A61F 2002/3055* (2013.01); *A61F 2002/30565* (2013.01); *A61F 2002/30688* (2013.01); *A61F 2/389* (2013.01)

(58) Field of Classification Search
CPC .. A61F 2002/30556; A61F 2002/30579; A61F 2002/30688
See application file for complete search history.

(56) References Cited

U.S. PATENT DOCUMENTS

| | | | |
|---|---|---|---|
| 3,886,599 A | 6/1975 | Schlein |
| 3,889,300 A | 6/1975 | Smith |
| 3,964,106 A | 6/1976 | Hutter et al. |
| 4,007,495 A | 2/1977 | Frazier |
| 4,041,550 A | 8/1977 | Frazier |
| 4,052,753 A | 10/1977 | Dedo |
| 4,069,518 A | 1/1978 | Groth et al. |
| 4,156,944 A | 6/1979 | Schreiber et al. |
| 4,158,894 A | 6/1979 | Worrell |
| 4,164,793 A | 8/1979 | Swanson |
| 4,285,070 A | 8/1981 | Averill |
| 4,470,158 A | 9/1984 | Pappas et al. |
| 4,642,122 A | 2/1987 | Steffee |
| 4,650,490 A | 3/1987 | Figgie |
| 4,759,766 A | 7/1988 | Buettner Janz et al. |
| 4,904,261 A | 2/1990 | Dove et al. |
| 4,955,915 A | 9/1990 | Swanson |
| 5,019,104 A | 5/1991 | Whiteside et al. |
| 5,035,700 A | 7/1991 | Kenna |
| 5,152,790 A | 10/1992 | Rosenberg et al. |
| 5,197,986 A | 3/1993 | Mikhail |
| 5,231,977 A | 8/1993 | Graston |
| 5,258,032 A | 11/1993 | Bertin |
| 5,314,481 A | 5/1994 | Bianco |
| 5,326,364 A | 7/1994 | Clift et al. |
| 5,383,937 A | 1/1995 | Mikhail |
| 5,425,775 A | 6/1995 | Kovacevic et al. |
| 5,480,443 A | 1/1996 | Elias |
| 5,544,993 A | 8/1996 | Harle |
| 5,545,229 A | 8/1996 | Parsons et al. |
| 5,571,139 A | 11/1996 | Jenkins |
| 5,571,198 A | 11/1996 | Drucker et al. |
| 5,580,353 A | 12/1996 | Mendes et al. |
| 5,643,272 A | 7/1997 | Haines et al. |
| 5,676,667 A | 10/1997 | Hausman |
| 5,702,460 A | 12/1997 | Carls et al. |
| 5,702,465 A | 12/1997 | Burkinshaw |
| 5,702,467 A | 12/1997 | Gabriel et al. |
| 5,733,287 A | 3/1998 | Tepic et al. |
| 5,824,106 A | 10/1998 | Fournol |
| 5,879,386 A | 3/1999 | Jore |
| 5,888,203 A | 3/1999 | Goldberg |
| 6,132,468 A | 10/2000 | Mansmann |
| 6,143,032 A | 11/2000 | Schafer et al. |
| 6,146,423 A | 11/2000 | Cohen et al. |
| 6,200,347 B1 | 3/2001 | Anderson et al. |
| 6,245,110 B1 | 6/2001 | Grundei et al. |
| 6,280,474 B1 | 8/2001 | Cassidy et al. |
| 6,302,915 B1 | 10/2001 | Cooney et al. |
| 6,315,798 B1 | 11/2001 | Ashby et al. |
| 6,368,326 B1 | 4/2002 | Dakin et al. |
| 6,371,985 B1 | 4/2002 | Goldberg |
| 6,409,767 B1 | 6/2002 | Pericéet al. |
| 6,468,314 B2 | 10/2002 | Schwartz et al. |
| 6,520,964 B2 | 2/2003 | Tallarida et al. |
| 6,527,794 B1 | 3/2003 | McDevitt et al. |
| 6,579,318 B2 | 6/2003 | Varga et al. |
| 6,589,248 B1 | 7/2003 | Hughes |
| 6,592,622 B1 | 7/2003 | Ferguson |
| 6,599,321 B2 | 7/2003 | Hyde |
| 6,616,696 B1 | 9/2003 | Merchant |
| 6,626,945 B2 | 9/2003 | Simon et al. |
| 6,632,247 B2 | 10/2003 | Boyer et al. |
| 6,679,914 B1 | 1/2004 | Gabbay |
| 6,702,821 B2 | 3/2004 | Bonutti |
| 6,709,460 B2 | 3/2004 | Merchant |
| 6,712,856 B1 | 3/2004 | Carignan et al. |
| 6,719,794 B2 | 4/2004 | Gerber et al. |
| 6,800,094 B2 | 10/2004 | Burkinshaw |
| 6,814,757 B2 | 11/2004 | Kopylov et al. |
| 6,824,567 B2 | 11/2004 | Tomier et al. |
| 6,852,330 B2 | 2/2005 | Bowman et al. |
| 6,854,330 B2 | 2/2005 | Potter |
| 6,855,150 B1 | 2/2005 | Linehan |
| 6,866,684 B2 | 3/2005 | Fell et al. |
| 6,890,358 B2 | 5/2005 | Ball et al. |
| 6,893,463 B2 | 5/2005 | Fell et al. |
| 6,896,702 B2 | 5/2005 | Collazo |
| 6,905,513 B1 | 6/2005 | Metzger |
| 6,911,044 B2 | 6/2005 | Fell et al. |
| 6,916,341 B2 | 7/2005 | Rolston |
| 6,926,739 B1 | 8/2005 | O'Connor et al. |
| 6,966,928 B2 | 11/2005 | Fell et al. |
| 6,974,480 B2 | 12/2005 | Messerli et al. |
| 6,994,730 B2 | 2/2006 | Posner |
| 7,004,971 B2 | 2/2006 | Serhan et al. |
| 7,008,452 B2 | 3/2006 | Hawkins |
| 7,011,687 B2 | 3/2006 | Deffenbaugh et al. |
| 7,025,790 B2 | 4/2006 | Parks et al. |
| 7,060,073 B2 | 6/2006 | Frey et al. |
| 7,105,025 B2 | 9/2006 | Castro et al. |
| 7,105,027 B2 | 9/2006 | Lipman et al. |
| 7,124,762 B2 | 10/2006 | Carter et al. |
| 7,160,333 B2 | 1/2007 | Plouhar et al. |
| 7,163,563 B2 | 1/2007 | Schwartz et al. |
| 7,182,787 B2 | 2/2007 | Hassler et al. |
| 7,226,482 B2 | 6/2007 | Messerli et al. |
| 7,291,169 B2 | 11/2007 | Hodorek |
| 7,297,161 B2 | 11/2007 | Fell |
| 7,323,012 B1 | 1/2008 | Stone et al. |
| 7,341,602 B2 | 3/2008 | Fell et al. |
| 7,476,225 B2 | 1/2009 | Cole |
| 7,479,160 B2 | 1/2009 | Branch et al. |
| 7,485,147 B2 | 2/2009 | Pappas et al. |
| 7,500,991 B2 | 3/2009 | Bartish et al. |
| 7,534,270 B2 | 5/2009 | Ball |
| 7,544,210 B2 | 6/2009 | Schaefer et al. |
| 7,572,291 B2 | 8/2009 | Gil et al. |
| 7,618,454 B2 | 11/2009 | Bentley et al. |
| 7,632,311 B2 | 12/2009 | Seedhom et al. |
| 7,637,953 B2 | 12/2009 | Branch et al. |
| 7,641,689 B2 | 1/2010 | Fell et al. |
| 7,722,676 B2 | 5/2010 | Hanson et al. |
| 7,723,395 B2 | 5/2010 | Ringeisen et al. |
| 7,726,319 B1 | 6/2010 | Boyce |
| 7,749,276 B2 | 7/2010 | Fitz |
| 7,758,651 B2 | 7/2010 | Chauhan et al. |
| 7,780,670 B2 | 8/2010 | Bonutti |
| 7,806,898 B2 | 10/2010 | Justin et al. |
| 7,815,645 B2 | 10/2010 | Haines |
| 7,819,918 B2 | 10/2010 | Malaviya et al. |
| 7,875,082 B2 | 1/2011 | Naidu |
| 7,879,105 B2 | 2/2011 | Schmieding et al. |
| 7,896,921 B2 | 3/2011 | Smith et al. |
| 7,896,923 B2 | 3/2011 | Blackwell et al. |
| 7,959,675 B2 | 6/2011 | Gately |
| 7,967,863 B2 | 6/2011 | Frey et al. |
| 7,972,383 B2 | 7/2011 | Goldstein et al. |
| 7,993,402 B2 | 8/2011 | Sidler |
| 8,002,833 B2 | 8/2011 | Fabris Monterumici et al. |
| 8,002,837 B2 | 8/2011 | Stream et al. |
| 8,002,841 B2 | 8/2011 | Hasselman |
| 8,034,117 B2 | 10/2011 | Matsuzaki et al. |
| 8,043,375 B2 | 10/2011 | Strzepa et al. |
| 8,043,380 B1 | 10/2011 | Park et al. |
| 8,052,753 B2 | 11/2011 | Melvin |
| 8,052,755 B2 | 11/2011 | Naidu |
| 8,083,746 B2 | 12/2011 | Novak |
| 8,088,168 B2 | 1/2012 | Hassler et al. |
| 8,092,544 B2 | 1/2012 | Wright et al. |
| 8,114,156 B2 | 2/2012 | Hatch |
| 8,128,704 B2 | 3/2012 | Brown et al. |
| 8,142,503 B2 | 3/2012 | Malone |

(56) References Cited

U.S. PATENT DOCUMENTS

| | | |
|---|---|---|
| 8,257,444 B2 | 9/2012 | Linares |
| 8,372,078 B2 | 2/2013 | Collazo |
| 8,597,362 B2 | 12/2013 | Shenoy et al. |
| 9,114,016 B2 * | 8/2015 | Shenoy .............. A61B 17/8872 |
| 9,278,004 B2 | 3/2016 | Shenoy et al. |
| 9,808,287 B2 | 11/2017 | Halbrecht |
| 9,808,289 B2 | 11/2017 | Ross et al. |
| 10,034,679 B1 | 7/2018 | Boyer et al. |
| 10,918,415 B2 | 2/2021 | Halbrecht |
| 10,918,416 B2 | 2/2021 | Halbrecht |
| 2001/0023371 A1 | 9/2001 | Bonutti |
| 2002/0029084 A1 | 3/2002 | Paul et al. |
| 2002/0091447 A1 | 7/2002 | Shimp et al. |
| 2002/0107574 A1 | 8/2002 | Boehm et al. |
| 2002/0133230 A1 | 9/2002 | Repicci |
| 2003/0083751 A1 | 5/2003 | Tornier |
| 2003/0088315 A1 | 5/2003 | Supinski |
| 2003/0100950 A1 | 5/2003 | Moret |
| 2003/0109928 A1 | 6/2003 | Pasquet et al. |
| 2003/0120344 A1 | 6/2003 | Michelson |
| 2003/0120346 A1 | 6/2003 | Mercinek et al. |
| 2003/0125807 A1 | 7/2003 | Lambrecht et al. |
| 2003/0138329 A1 | 7/2003 | Koyano et al. |
| 2003/0171757 A1 | 9/2003 | Coon et al. |
| 2003/0204265 A1 | 10/2003 | Short et al. |
| 2004/0039395 A1 | 2/2004 | Coon et al. |
| 2004/0117020 A1 | 6/2004 | Frey et al. |
| 2004/0133278 A1 | 7/2004 | Marino et al. |
| 2004/0143336 A1 | 7/2004 | Burkinshaw |
| 2004/0143338 A1 | 7/2004 | Burkinshaw et al. |
| 2004/0186585 A1 | 9/2004 | Feiwell |
| 2004/0215195 A1 | 10/2004 | Shipp et al. |
| 2004/0230303 A1 | 11/2004 | Gomes et al. |
| 2004/0230315 A1 | 11/2004 | Ek |
| 2004/0236428 A1 | 11/2004 | Burkinshaw et al. |
| 2004/0243240 A1 | 12/2004 | Beaurain et al. |
| 2005/0004671 A1 | 1/2005 | Ross et al. |
| 2005/0027360 A1 | 2/2005 | Webb et al. |
| 2005/0033424 A1 | 2/2005 | Fell |
| 2005/0033426 A1 | 2/2005 | Ogilvie et al. |
| 2005/0137708 A1 | 6/2005 | Clark |
| 2005/0143822 A1 | 6/2005 | Paul |
| 2005/0222685 A1 | 10/2005 | Hayden et al. |
| 2005/0267584 A1 | 12/2005 | Burdulis et al. |
| 2005/0288788 A1 | 12/2005 | Dougherty Shah |
| 2006/0036321 A1 | 2/2006 | Henninger et al. |
| 2006/0074423 A1 | 4/2006 | Alleyne et al. |
| 2006/0074492 A1 | 4/2006 | Frey |
| 2006/0100715 A1 | 5/2006 | De Villiers |
| 2006/0129243 A1 | 6/2006 | Wong et al. |
| 2006/0142858 A1 | 6/2006 | Colleran et al. |
| 2006/0161260 A1 | 7/2006 | Thomas et al. |
| 2006/0276907 A1 | 12/2006 | Boyer et al. |
| 2007/0027547 A1 | 2/2007 | Rydell et al. |
| 2007/0129809 A1 | 6/2007 | Meridew et al. |
| 2007/0173946 A1 | 7/2007 | Bonutti |
| 2007/0203581 A1 | 8/2007 | Vanaclocha |
| 2007/0208343 A1 | 9/2007 | Magert et al. |
| 2007/0233141 A1 | 10/2007 | Park et al. |
| 2007/0265708 A1 | 11/2007 | Brown et al. |
| 2007/0293947 A1 | 12/2007 | Mansmann |
| 2007/0299528 A9 | 12/2007 | Lotke |
| 2008/0021566 A1 | 1/2008 | Peters et al. |
| 2008/0091270 A1 | 4/2008 | Miller et al. |
| 2008/0097617 A1 | 4/2008 | Fellinger et al. |
| 2008/0140094 A1 | 6/2008 | Schwartz et al. |
| 2008/0154267 A1 | 6/2008 | Merchant et al. |
| 2008/0154311 A1 | 6/2008 | Staeubli |
| 2008/0154371 A1 | 6/2008 | Fell et al. |
| 2008/0161815 A1 | 7/2008 | Schoenefeld et al. |
| 2008/0161933 A1 | 7/2008 | Grotz et al. |
| 2008/0172054 A1 | 7/2008 | Claypool et al. |
| 2008/0195099 A1 | 8/2008 | Minas |
| 2008/0234762 A1 | 9/2008 | Forstein et al. |
| 2008/0262618 A1 | 10/2008 | Hermsen et al. |
| 2008/0281422 A1 | 11/2008 | Schmieding |
| 2008/0281425 A1 | 11/2008 | Thalgott et al. |
| 2009/0012615 A1 | 1/2009 | Fell |
| 2009/0088763 A1 | 4/2009 | Aram et al. |
| 2009/0088846 A1 | 4/2009 | Myung et al. |
| 2009/0118830 A1 | 5/2009 | Fell |
| 2009/0130167 A1 | 5/2009 | Shelton et al. |
| 2009/0164014 A1 | 6/2009 | Liljensten et al. |
| 2009/0182433 A1 | 7/2009 | Reiley et al. |
| 2009/0198341 A1 | 8/2009 | Choi et al. |
| 2009/0210063 A1 | 8/2009 | Barrett |
| 2009/0226068 A1 | 9/2009 | Fitz et al. |
| 2009/0259311 A1 | 10/2009 | Shterling et al. |
| 2009/0259312 A1 | 10/2009 | Shterling et al. |
| 2009/0306783 A1 | 12/2009 | Blum |
| 2009/0312807 A1 | 12/2009 | Boudreault et al. |
| 2010/0023126 A1 | 1/2010 | Grotz |
| 2010/0049322 A1 | 2/2010 | McKay |
| 2010/0049325 A1 | 2/2010 | Biedermann et al. |
| 2010/0057216 A1 | 3/2010 | Gannoe et al. |
| 2010/0121355 A1 | 5/2010 | Gittings et al. |
| 2010/0125266 A1 | 5/2010 | Deem et al. |
| 2010/0131069 A1 | 5/2010 | Halbrecht |
| 2010/0161057 A1 | 6/2010 | Berry et al. |
| 2010/0198354 A1 | 8/2010 | Halbrecht |
| 2010/0204798 A1 | 8/2010 | Gerbec et al. |
| 2010/0262246 A1 | 10/2010 | Attia |
| 2010/0292731 A1 | 11/2010 | Gittings et al. |
| 2010/0292733 A1 | 11/2010 | Hendricksen et al. |
| 2010/0305698 A1 | 12/2010 | Metzger et al. |
| 2011/0004305 A1 | 1/2011 | Jansson et al. |
| 2011/0054627 A1 | 3/2011 | Bear |
| 2011/0093073 A1 | 4/2011 | Gatt et al. |
| 2011/0172768 A1 | 7/2011 | Cragg et al. |
| 2011/0202138 A1 * | 8/2011 | Shenoy .................... A61F 2/32 |
| | | 623/20.14 |
| 2011/0213466 A1 | 9/2011 | Shenoy et al. |
| 2011/0238180 A1 | 9/2011 | Fritz et al. |
| 2011/0264216 A1 | 10/2011 | Makower et al. |
| 2011/0270393 A1 | 11/2011 | Marvel |
| 2011/0288643 A1 | 11/2011 | Linder-Ganz et al. |
| 2012/0022649 A1 | 1/2012 | Robinson et al. |
| 2012/0065640 A1 | 3/2012 | Metzger et al. |
| 2012/0191204 A1 | 7/2012 | Bae et al. |
| 2013/0060343 A1 | 3/2013 | Halbrecht |
| 2013/0131802 A1 | 5/2013 | Halbrecht |
| 2013/0150977 A1 | 6/2013 | Gabriel et al. |
| 2013/0190886 A1 | 7/2013 | Tepic et al. |
| 2013/0304208 A1 | 11/2013 | Clifford et al. |
| 2014/0277444 A1 | 9/2014 | Clifford et al. |
| 2015/0196325 A1 | 7/2015 | Shenoy et al. |
| 2018/0028229 A1 | 2/2018 | Halbrecht |
| 2018/0214261 A1 | 8/2018 | Treacy et al. |
| 2019/0099273 A1 | 4/2019 | Servidio |
| 2021/0205067 A1 | 7/2021 | Shulock et al. |
| 2021/0205068 A1 | 7/2021 | Shulock et al. |

OTHER PUBLICATIONS

Gaasbeek et al.; The influence of open and closed high tibial osteotomy on dynamic patellar tracking: a biomechanical study; Knee surg. Sports Traumatol. Arthrosc.; 15(8); pp. 978-984; Aug. 1, 2007.

Maquet; Biomechanical treatment of patellofemoral osteoarthritis. Advancement of the patellar tendon: review of rheumatism and osteoarticular diseases, National Library of Medicine; vol. 30; issue 12; pp. 780-785; (year of pub. sufficiently earlier than effective US filing date and any foreign priority date) 1963.

Zimmer; Nex Gen trabecular metal augmentation patella, Surgical technique; 4 pages; retrieved from the internet (http://www.zimmer.com/content/dam/zimmer-web/documents/en-US/pdf/surgical-techniques/knee/NexGen-Trabecular-Metal-Augmentation-Patella-Surgical-Technique-97-7255-004-00-Rev-24-2008.pdf) on Dec. 29, 2017.

* cited by examiner

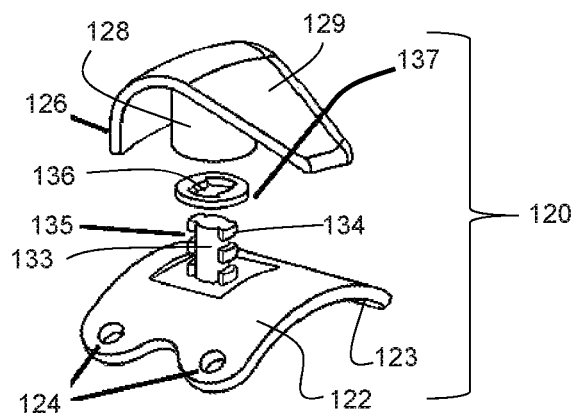
FIG. 12
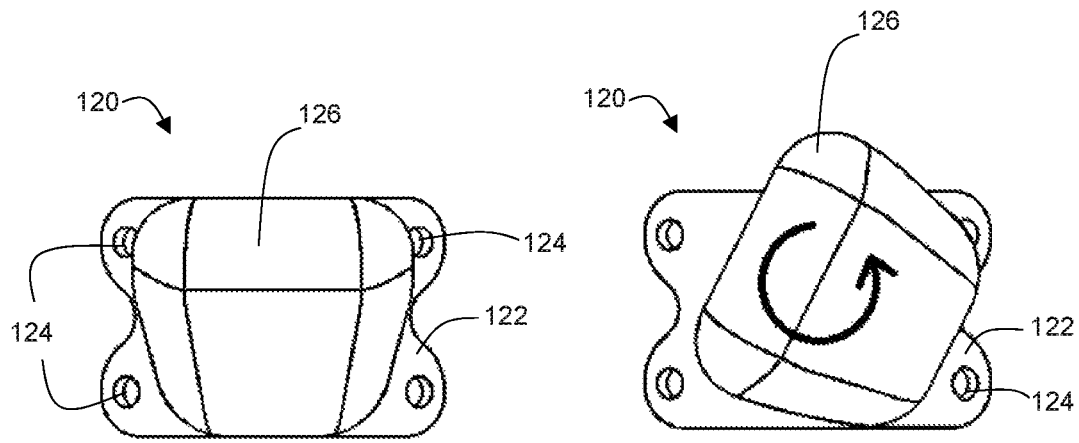
FIG. 13
FIG. 14

ADJUSTABLE PATELLAR TENDON REALIGNMENT IMPLANT

CROSS REFERENCE TO RELATED APPLICATIONS

This application claims the benefit of priority of U.S. Provisional Application No. 63/022,977, filed May 11, 2020, herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Problems of the patella-femoral joint are a common cause of knee pain. The pain may arise from issues such as poor alignment of the patella or from cartilage breakdown (chondromalacia or arthritis) behind the patella or on the opposing articular surface of the femoral groove (trochlea). Conventional surgical options for treating patella-femoral pain caused by malalignment, chondromalacia or arthritis may include realignment of the patella. For example tracking of the patella may be changed by tilting the patella or by moving the patella to one side or the other. Moving the patella forward (i.e., anteriorly) through a surgical procedure provides another conventional option for treating these conditions. This conventional technique is thought to decrease force across the patella-femoral joint and thus diminish the pain arising from excess force against a worn-out patellar or trochlear cartilage.

Although available, surgical options to realign the patella may be very invasive. For example, surgeries may involve cutting and fixating the bony attachment of the patellar tendon. In particular, conventional techniques may include detaching the patellar tendon from the tibia, then reattaching the patellar tendon at a new location to obtain the desired alignment of the patella. Such invasive surgical techniques may also result in prolonged recovery times. Consequently, an improved mechanism for treating patella-femoral joint problems such as patella-femoral pain, chondromalacia, and/or arthritis is desired.

U.S. Pat. No. 9,808,289 discloses embodiments of a patellar tendon realignment implant configured to be placed between the patellar tendon and the tibia in proximity to the patella to elevate and/or tilt the patellar tendon. Each of the implants has a fixed height and cannot be adjusted prior to, or after, implantation to meet the patient's needs.

SUMMARY OF THE DISCLOSURE

Some activities result in higher tension or compression of the patellar tendon. For example, stair climbing and jumping increase the tension on the patellar tendon, and kneeling or sudden impacts to the knee increase patellar tendon compression. It may be desirable to temporarily change the shape of a patellar tendon realignment implant during application of a tension load on the patellar tendon (e.g., during stair climbing, jumping, etc.) or application of a compression load on the patellar tendon (e.g., during kneeling, a sudden impact to the knee, etc.).

One aspect of the invention provides an orthopedic implant with an inferior portion having a tibia contact surface configured to extend over a tibia; a superior portion opposite to the inferior portion having a tendon contact surface configured to change a position of a patellar tendon by lifting or tilting the patellar tendon when the curved surface of the first portion is engaged with the tibia; a fixation mechanism adapted to attach the orthopedic implant to the tibia; and an adjustment mechanism adapted to change a distance between the tendon contact surface and the tibia contact surface.

In some embodiments, the orthopedic implant also has a hinge or pivot connecting the superior portion to the inferior portion.

In some embodiments, the adjustment mechanism includes a piston disposed between the superior portion and the inferior portion. In some such embodiments, the adjustment mechanism includes a port fluidly connected with an interior of the piston through which fluid can be added or removed from the interior of the piston. In other such embodiments, the piston has a threaded connection between a superior piston element and an inferior piston element.

In some embodiments, the adjustment mechanism includes a rotatable cam disposed between the superior portion and the inferior portion.

In some embodiments, the adjustment mechanism includes an adjustable connection between the superior portion and the inferior portion adapted and configured to enable a user to move the superior portion along a ramp to change the distance between the tendon contact surface and the tibia contact surface. In some such embodiments, the adjustment mechanism includes a sliding connection between the ramp and the superior portion, wherein moving the superior portion along the sliding connection changes the distance between the tendon contact surface and the tibia contact surface. In some or all such embodiments, the adjustment mechanism also has a lock with a first configuration adapted to hold a position of the superior portion with respect to the inferior portion and a second configuration adapted to permit the superior portion to be moved with respect to the inferior portion.

In some embodiments, the adjustment mechanism comprises a column fixed to, and extending up from, the inferior portion, and a plurality of connection slots to which the superior portion can be selectively engaged. In some such embodiments, the adjustment mechanism also has a tab supported by the superior portion and biased by a spring, the spring biasing the tab into one of the connection slots to prevent relative movement between the superior portion and the inferior portion, the tab being movable against the spring out of the one of the connection slots to permit movement of the superior portion with respect to the inferior portion. The orthopedic implant may also have a button operatively connected to the tab to move the tab against the spring. In other such embodiments, the adjustment mechanism further has a rotatable connection between the superior portion and the column, the rotatable connection having a first position permitting movement of the superior portion to a second connection position and a second position preventing movement of the superior portion from the first connection position to the second connection position.

In some embodiments, the orthopedic implant has a sealed cavity disposed between the superior portion and the inferior portion, the adjustment mechanism comprising a port in fluid communication with the sealed cavity.

Another aspect of the invention provides a method for repositioning a patellar tendon of a patient. In some embodiments, the method includes the steps of inserting an orthopedic implant in a first configuration between the patellar tendon and a tibia; engaging a tibia contact surface of an inferior portion of the orthopedic implant with the tibia; engaging a tendon contact surface of a superior portion of the orthopedic implant with the patellar tendon; changing a distance between the tendon contact surface and the tibia contact surface; and changing a position of the patellar tendon In some embodiments, the step of changing a distance between the tendon contact surface and the tibia contact surface is performed after the steps of engaging the tibia contact surface with the tibia and engaging the tendon contact surface with the patellar tendon. In some such embodiments, the changing step includes the step of inserting a tool through a skin opening to engage an adjustment mechanism. Such methods may also include the step of piercing the skin with the tool.

In some embodiments, the step of changing a distance between the tendon contact surface and the tibia contact surface includes the step of moving the superior portion along a ramp.

In some embodiments in which a first end of the superior portion is connected to the inferior portion with a hinge or pivot, the step of changing a distance between the tendon contact surface and the tibia contact surface includes the step of moving a second end of the superior portion about the hinge or pivot.

In some embodiments, the step of changing a distance between the tendon contact surface and the tibia contact surface comprises changing a height of a piston extending between the superior portion and the inferior portion, such as by changing the height of the piston comprises adding or removing fluid from an interior of the piston or rotating a ring engaged with threads on the piston.

In some embodiments, the step of changing a distance between the tendon contact surface and the tibia contact surface includes the step of changing a position of a cam disposed between the superior portion and the inferior portion.

In embodiments in which the orthopedic implant has a column disposed between the inferior portion and the superior portion, the step of changing a distance between the tendon contact surface and the tibia contact surface may include the step of disengaging a tab from a slot in the column. In some such embodiments, the step of disengaging a tab from a slot in the column includes the step of moving the tab against a spring, and the step of changing a distance between the tendon contact surface and the tibia contact surface includes the step of permitting the spring to move the tab back into a slot of the column. In other such embodiments, the step of disengaging a tab from a slot in the column includes the step of rotating the superior portion with respect to the inferior portion.

In embodiments in which the orthopedic implant has an expandable cavity disposed between the tendon contact surface and the tibia contact surface, the step of changing a distance between the tendon contact surface and the tibia contact surface may include the step of adding or removing fluid from the expandable cavity.

In some embodiments, the step of changing a distance between the tendon contact surface and the tibia contact surface is performed before the steps of engaging the tibia contact surface with the tibia and engaging the tendon contact surface with the patellar tendon.

Some embodiments include the further step of locking the orthopedic implant after changing the distance between the tendon contact surface and the tibia contact surface.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 12 is an exploded view of an orthopedic implant according to yet another embodiment of the invention.

FIG. 13 is a top view of the orthopedic implant of FIG. 12 in a locked position.

FIG. 14 is a top view of the orthopedic implant of FIG. 12 in an unlocked position.

DETAILED DESCRIPTION

Figure 1A:
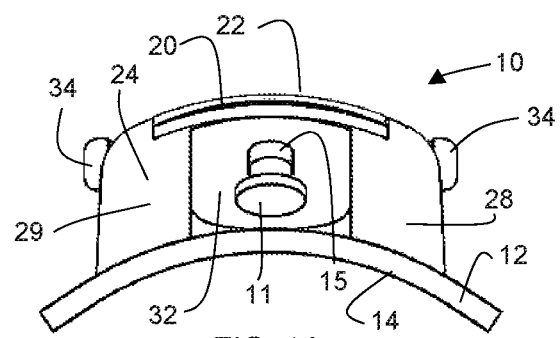
FIG. 1A is an end view of an orthopedic implant according to an embodiment of the invention in an unextended position.
Figure 1B:
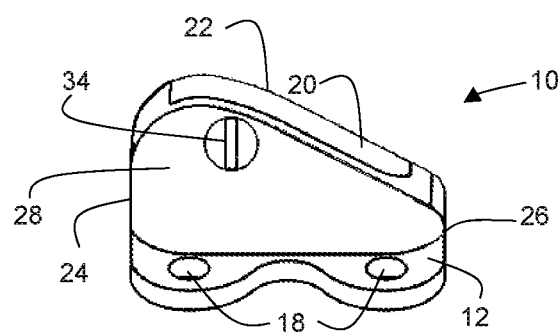
FIG. 1B is a side view of the orthopedic implant of FIG. 1A.
Figure 2A:
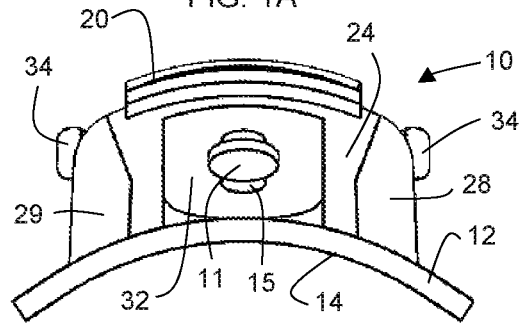
FIG. 2A is an end view of the orthopedic implant of FIG. 1 in an extended position.
Figure 2B:
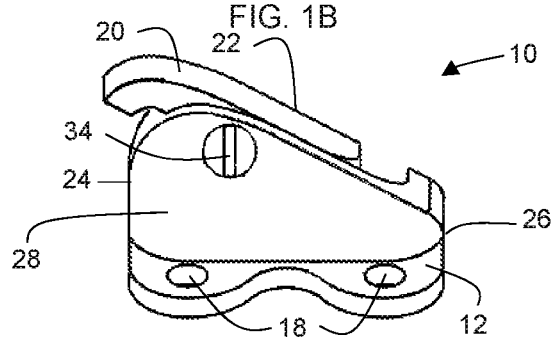
FIG. 2B is a side view of the orthopedic implant of FIG. 2A
Figure 3:
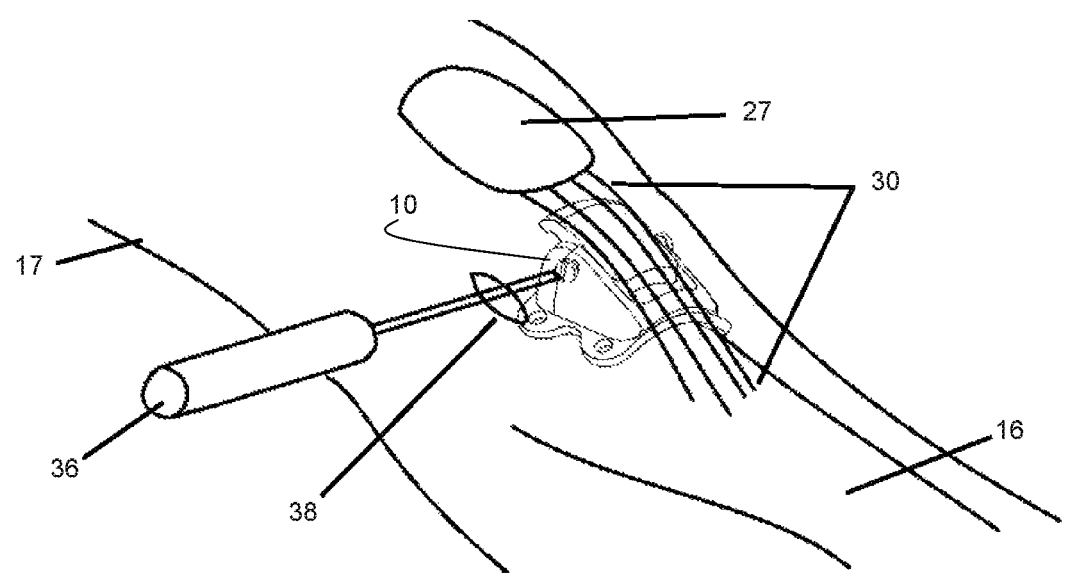
FIG. 3 shows the orthopedic implant of FIGS. 2A-2B in place on a patient.

FIGS. 1-3 show one embodiment of an adjustable orthopedic implant for use in adjusting the height of a patellar tendon. Orthopedic implant 10 has an inferior portion 12 with a tibia contact surface 14 adapted to engage the patient's tibia 16 in the patient's leg 17. Holes 18 on both sides of the inferior portion are sized to receive screws or other fixation devices to attach the implant to the tibia 16.

The superior portion 20 of the implant has a tendon contact surface 22 on its top side. Two side portions 28 and 29 extend between the inferior portion and the superior portion. In this embodiment, the anterior end 24 of the implant 10 is taller than the posterior end 26 of the implant. When in place on the patient, the anterior end 24 is placed closer to the patient's patella 27 than the posterior end 26 is, as shown in FIG. 3. The patellar tendon 30 rests on the tendon contact surface 22.

Superior portion 20 may be extended or retracted along a ramp 32 extending between the side portions 28 and 29 to change the distance between the tibia contact surface and the tendon contact surface by changing the effective height of the anterior end of the implant in order to provide the desired upward lift of the patellar tendon. A pin 11 extending from superior portion 20 through a slot 15 in the ramp 32 limits the motion of superior portion 20 along the ramp 32. Thereafter, locks 34 (such as, e.g., a movable screw) may be engaged to prevent further movement. The implant's effective height may be set prior to implantation, or, as shown in FIG. 3, the position of the superior portion may be changed after implantation. A tool 36 may be inserted through an incision 38 to access the locks 34. The orthopedic implant of FIGS. 1-3 may be made of any suitable material (e.g., rigid metals and/or plastics).

FIGS. 4-7 show embodiments of orthopedic implants according to this invention in which the superior portion connects to the inferior portion via a pivot or hinge. Changes in the implant height change the distance between the tendon contact surface and the tibia contact surface.

Figure 4:
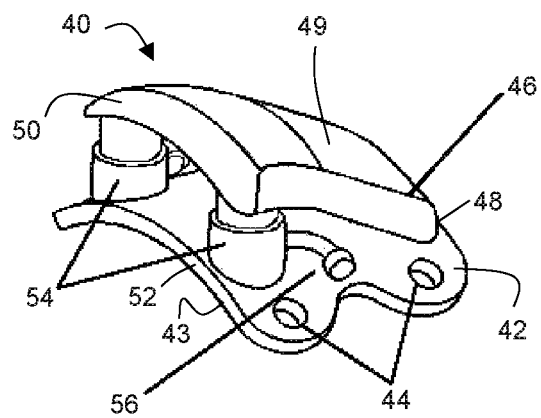
FIG. 4 is a perspective view of an orthopedic implant according to another embodiment of the invention.

The orthopedic implant 40 of FIG. 4 has an inferior portion 42 with a tibia contact surface 43 adapted to engage a patient's tibia. Holes 44 on both sides of the inferior portion are sized to receive screws or other fixation devices to attach the implant to the tibia. Superior portion 46 of orthopedic implant 40 is connected to the inferior portion 42 via a pivot or hinge at the posterior end 48 of the implant. Superior portion 46 has a tendon contact surface 49 on its top side. The anterior end 50 of the superior portion 46 may be raised or lowered with respect to the anterior end 52 of the inferior portion 42 by increasing or decreasing the height of pistons 54. Fluid (such as saline solution) may be added to interior chambers of the pistons 54 through an access ports 56 (only one of which is shown in FIG. 4) to increase the height of the pistons, thereby rotating the anterior end of the superior portion about the pivot or hinge, increasing the height of the anterior end of the implant and raising the patellar tendon. Fluid may be extracted from the pistons' interior chambers to decrease their height, thereby decreasing the height of the anterior end of the implant and decreasing the amount of patellar tendon lift. This adjustment to the height of the implant may be performed prior to implantation of the implant and affixation of the implant to the tibia. The implant's height may also be adjusted after implantation and affixation by inserting the fluid line through an incision in the patient's leg and connecting the fluid line with the access ports 56. The orthopedic implant of FIG. 4 may be made of any suitable material (e.g., rigid metals and/or plastics).

Figure 5:
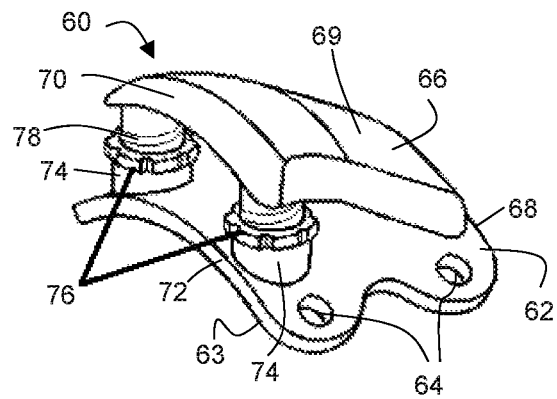
FIG. 5 is a perspective view of an orthopedic implant according to yet another embodiment of the invention.

FIG. 5 shows an orthopedic implant 60 with an inferior portion 62 and a tibia contact surface 63 adapted to engage a patient's tibia. Holes 64 on both sides of the inferior portion are sized to receive screws or other fixation devices to attach the implant to the tibia. Superior portion 66 of orthopedic implant 60 is connected to the inferior portion 62 via a pivot or hinge at the posterior end 68 of the implant. Superior portion 66 has a tendon contact surface 69 on its top side. The anterior end 70 of the superior portion 66 may be raised or lowered with respect to the anterior end 72 of the inferior portion 62 by increasing or decreasing the height of pistons 74. In this embodiment, the pistons' heights are adjusted by rotating a threaded ring 76 engaged with threads 78 in pistons 74. Once again, an increase in the height of the pistons rotates the anterior end of the superior portion about the pivot or hinge, increasing the height of the anterior end of the implant and raising the patellar tendon. A decrease in the pistons' height decreases the height of the anterior end of the implant and lowers the patellar tendon. This adjustment to the height of the implant, and consequent change in the distance between the tendon contact surface and the tibia contact surface, may be performed prior to or after implantation of the implant and affixation of the implant to the tibia. The orthopedic implant of FIG. 5 may be made of any suitable material (e.g., rigid metals and/or plastics).

Figure 6:
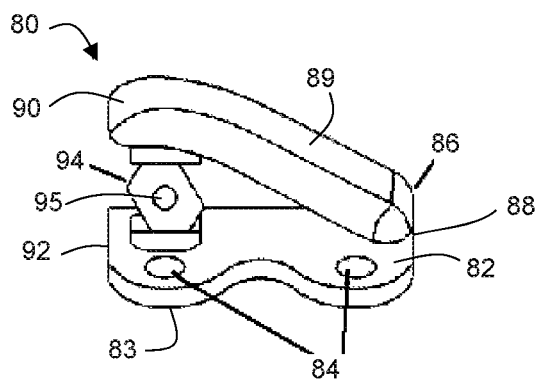
FIG. 6 is a perspective view of an orthopedic implant according to still another embodiment of the invention.
Figure 7:
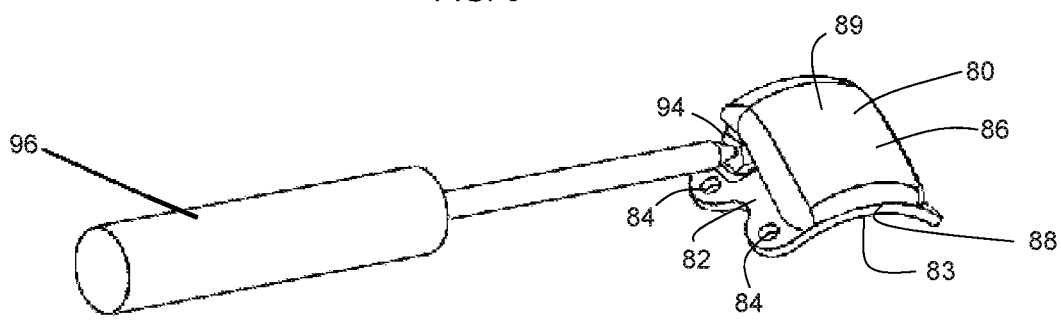
FIG. 7 is a perspective view of the orthopedic implant of FIG. 6 and an adjustment tool.
Figure 8:
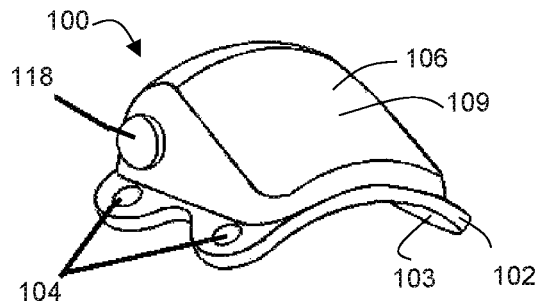
FIG. 8 is a perspective view of an orthopedic implant according to another embodiment of the invention.

The orthopedic implant 80 shown in FIGS. 6 and 7 has an inferior portion 82 and a tibia contact surface 83 adapted to engage a patient's tibia. Holes 84 on both sides of the inferior portion are sized to receive screws or other fixation devices to attach the implant to the tibia. Superior portion 86 of orthopedic implant 80 is connected to the inferior portion 82 via a pivot or hinge at the posterior end 88 of the implant. Superior portion 86 has a tendon contact surface 89 on its top side. The anterior end 90 of the superior portion 86 may be raised or lowered with respect to the anterior end 92 of the inferior portion 82 by rotating a cam 94 by engaging a hole 95 in cam 94 with a tool 96. Once again, a change in the implant's height changes the distance between the tendon contact surface and the tibia contact surface. An increase in the implant's height on the anterior end raises the patellar tendon, and a decrease in the height of the anterior end of the implant lowers the patellar tendon. This adjustment to the height of the implant may be performed prior to or after implantation of the implant and affixation of the implant to the tibia. The orthopedic implant of FIGS. 6-7 may be made of any suitable material (e.g., rigid metals and/or plastics).

Figure 9:
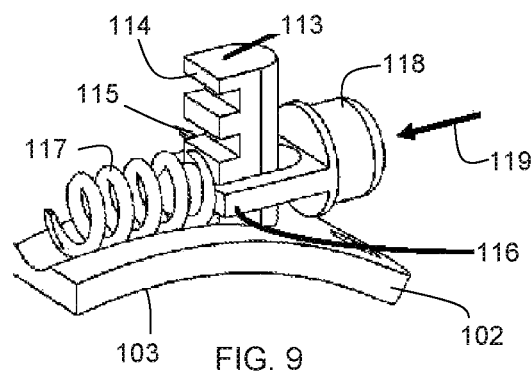
FIG. 9 is a perspective view part of the height adjustment mechanism of the orthopedic implant of FIG. 8.
Figure 10:
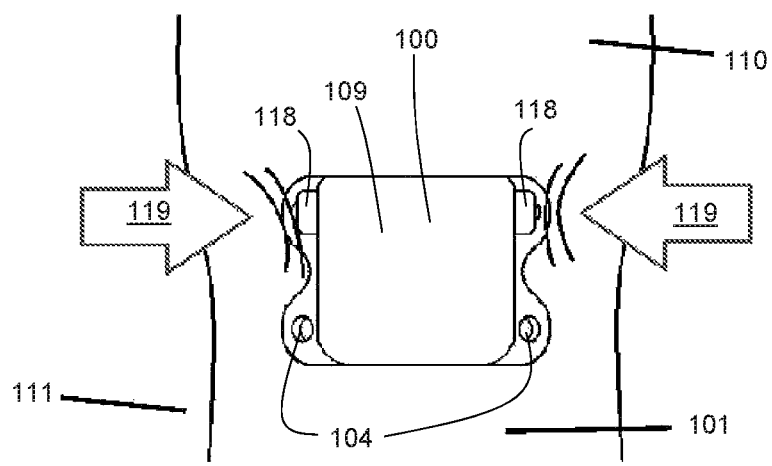
FIG. 10 shows the orthopedic implant of FIG. 8 after implantation on the patient.
Figure 11:
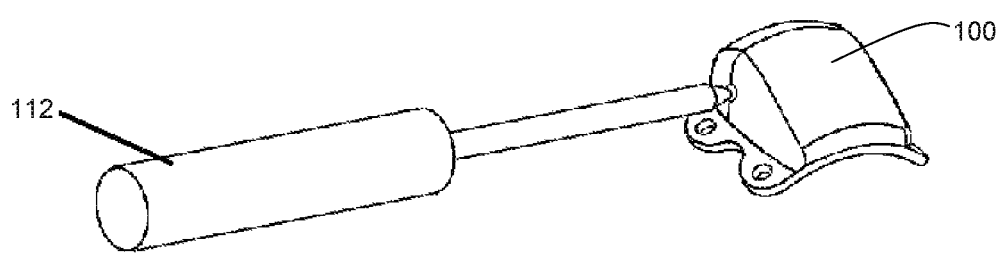
FIG. 11 is a perspective view of the orthopedic implant of FIG. 8 and an adjustment tool.

FIGS. 8-11 show yet another embodiment of an orthopedic implant according to this invention. Implant 100 has an inferior portion 102 and a tibia contact surface 103 adapted to engage a patient's tibia. Holes 104 on both sides of the inferior portion are sized to receive screws or other fixation devices to attach the implant to the tibia. Superior portion 106 has a tendon contact surface 109 on its top side. Two columns 113 (one of which is shown in FIG. 9) are affixed to the inferior portion 102 and extend upward within the superior portion 106. Columns 113 have alternating ridges 114 and slots 115. A tab 116 operatively connected to, and supported by, superior portion 106 is biased into one of the slots 115 by a spring 117. A button 118 connected to the tab 116 extends to the exterior of superior portion 106. When buttons 118 are pressed (as shown by arrows 119) to move tab 116 against the action of springs 117, tabs 116 move out of their respective slots 115, enabling the superior portion 106 to be raised or lowered with respect to the inferior portion 102. Releasing the buttons 118 permits the springs 117 to move their respective tabs 116 into slots 115 on columns 113 corresponding to the position to which the superior portion has been moved. The buttons may be depressed by a user's fingers or by using a tool 112, as shown in FIG. 11. As in the other embodiments, a change in the implant's height changes the distance between the tendon contact surface and the tibia contact surface. An increase in the implant's height raises the patellar tendon, and a decrease in the implant's height lowers the patellar tendon. This adjustment to the height of the implant may be performed prior to or after implantation of the implant and affixation of the implant to the tibia. For example, FIG. 10 shows implant 100 in place on the tibia 101 below the knee 110 in the patient's leg 111. The orthopedic implant of FIGS. 8-11 may be made of any suitable material (e.g., rigid metals and/or plastics).

The orthopedic implant 120 shown in FIGS. 12-14 has an inferior portion 122 and a tibia contact surface 123 adapted to engage a patient's tibia. Holes 124 on both sides of the inferior portion are sized to receive screws or other fixation devices to attach the implant to the tibia. Superior portion 126 has a tendon contact surface 129 on its top side. A column 133 is affixed to the inferior portion 122 and extends upward within the superior portion 126. Column 133 has corresponding ridges 134 and slots 135 on two opposing sides and no ridges or tabs on the other two opposing sides. Extending down from an inner surface of superior portion 126 is a hollow structure 128 with an oval-shaped opening 136 facing the inferior portion 122. As shown in the exploded view of FIG. 12 (in which the superior portion 126 is partially cut away for visibility), opening 136 is formed in a separate ring 137 that attaches to the bottom end of hollow structure 128. Other embodiments omit the ring, and the oval-shaped opening is integral with structure 128. Superior portion 126 may be rotated with respect to inferior portion 122, as shown in FIG. 14, to line up the long axis of oval-shaped opening 136 with ridges 134, thereby enabling superior portion 126 to be raised or lowered with respect to inferior portion 122. When the desired implant height is achieved, superior portion 126 is rotated back to the position shown in FIG. 13, which aligns the short axis of oval-shaped opening with the ridges 134 so that portions of the ring 137 on either side of the short axis sit between adjacent ridges, thereby locking the superior portion 126 in place. The portion of column 133 above the slots to which ring is engaged extends into the cavity of structure 128. As in the other embodiments, a change in the implant's height changes the distance between the tendon contact surface and the tibia contact surface. An increase in the implant's height raises the patellar tendon, and a decrease in the implant's height lowers the patellar tendon. This adjustment to the height of the implant may be performed prior to or after implantation of the implant and affixation of the implant to the tibia (by, e.g., manipulating the implant through the skin). The orthopedic implant of FIGS. 12-14 may be made of any suitable material (e.g., rigid metals and/or plastics).

Figure 15:
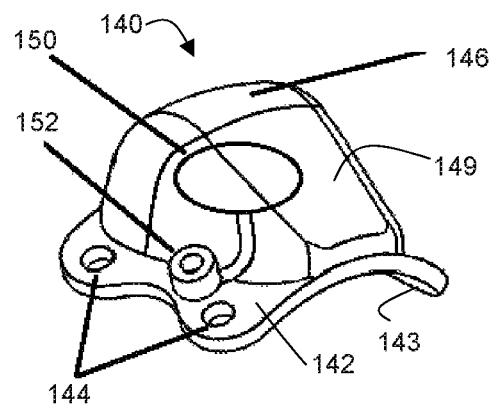
FIG. 15 is a perspective view of an orthopedic implant according to still another embodiment of the invention.
Figure 16:
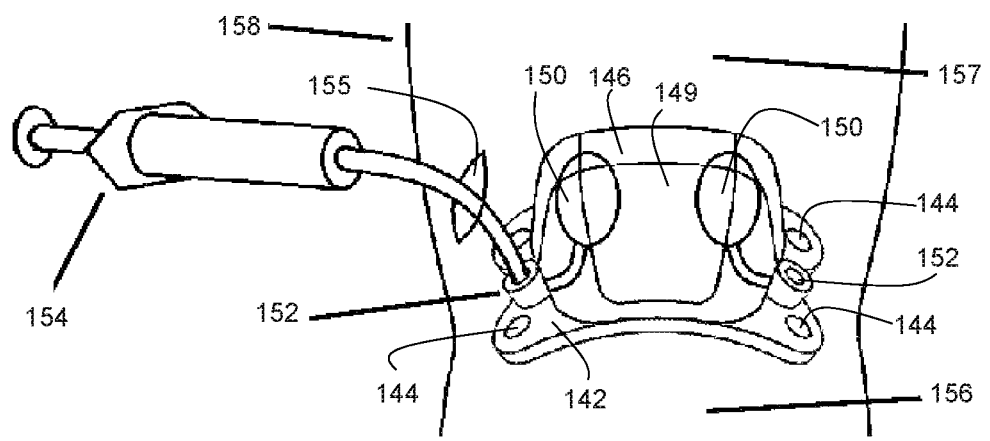
FIG. 16 is a perspective view of the orthopedic implant of FIG. 15 in place on a patient.

FIGS. 15 and 16 show yet another embodiment of an orthopedic implant according to this invention. Orthopedic implant 140 has an inferior portion 142 and a tibia contact surface 143 adapted to engage a patient's tibia. Holes 144 on both sides of the inferior portion are sized to receive screws or other fixation devices to attach the implant to the tibia. Superior portion 146 has a tendon contact surface 149 on its top side. In this embodiment, all or part of the superior portion 146 is made of a flexible material. One or more cavities 150 within the superior portion 146 beneath the tendon contact surface 149 communicate with sealing access ports 152. Fluid (e.g., air or saline) may be added or withdrawn from cavities 150 with a tool 154 engaged with access ports 152 to change the height of superior portion 146 with respect to the inferior portion 142, thereby changing the distance between the tendon contact surface 149 and tibia contact surface 143. This adjustment to the height of the implant may be performed prior to or after implantation of the implant and affixation of the implant to the tibia. As shown in FIG. 16, the tool 154 may be inserted through an incision 155 in the patient's leg 158 to the implant 140 in place on the patient's tibia 156 below the knee 157. The use of two cavities, as shown in FIG. 16, enables the height of the implant to be adjusted differently on the medial and lateral sides.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An orthopedic implant comprising:
   an inferior portion having a tibia contact surface configured to extend over a tibia;
   a superior portion opposite to the inferior portion and disposed between the patellar tendon and the inferior portion, the superior portion having a tendon contact surface configured to change a position of a patellar tendon by lifting or tilting the patellar tendon when a curved surface of the inferior portion is engaged with the tibia;
   a hinge or pivot connecting the superior portion to the inferior portion;
   a fixation mechanism adapted to attach the orthopedic implant to the tibia; and
   an adjustment mechanism adapted to change a distance between the tendon contact surface and the tibia contact surface.

2. An orthopedic implant comprising:
   an inferior portion having a tibia contact surface configured to extend over a tibia;
   a superior portion opposite to the inferior portion having a tendon contact surface configured to change a position of a patellar tendon by lifting or tilting the patellar tendon when the curved surface of the first portion is engaged with the tibia;
   a fixation mechanism adapted to attach the orthopedic implant to the tibia; and
   an adjustment mechanism adapted to change a distance between the tendon contact surface and the tibia contact surface, wherein the adjustment mechanism comprises a piston disposed between the superior portion and the inferior portion.

3. The orthopedic implant of claim 2 wherein the adjustment mechanism further comprises a port fluidly connected with an interior of the piston through which fluid can be added or removed from the interior of the piston.

4. The orthopedic implant of claim 2 wherein the piston comprises a threaded connection between a superior piston element and an inferior piston element.

5. An orthopedic implant comprising:
   an inferior portion having a tibia contact surface configured to extend over a tibia;
   a superior portion opposite to the inferior portion having a tendon contact surface configured to change a position of a patellar tendon by lifting or tilting the patellar tendon when the curved surface of the first portion is engaged with the tibia;
   a fixation mechanism adapted to attach the orthopedic implant to the tibia; and
   an adjustment mechanism adapted to change a distance between the tendon contact surface and the tibia contact surface, wherein the adjustment mechanism comprises a rotatable cam disposed between the superior portion and the inferior portion.

6. An orthopedic implant comprising:
   an inferior portion having a tibia contact surface configured to extend over a tibia;
   a superior portion opposite to the inferior portion having a tendon contact surface configured to change a position of a patellar tendon by lifting or tilting the patellar tendon when the curved surface of the first portion is engaged with the tibia;

a fixation mechanism adapted to attach the orthopedic implant to the tibia; and an adjustment mechanism adapted to change a distance between the tendon contact surface and the tibia contact surface, wherein the adjustment mechanism comprises:

an adjustable connection between the superior portion and the inferior portion adapted and configured to enable a user to move the superior portion along a ramp to change the distance between the tendon contact surface and the tibia contact surface; or a column fixed to, and extending up from, the inferior portion, and a plurality of connection slots to which the superior portion can be selectively engaged.

7. The orthopedic implant of claim 6 wherein the adjustable connection comprises a sliding connection between the ramp and the superior portion, wherein moving the superior portion along the sliding connection changes the distance between the tendon contact surface and the tibia contact surface.

8. The orthopedic implant of claim 6 wherein the adjustable connection further comprises a lock with a first configuration adapted to hold a position of the superior portion with respect to the inferior portion and a second configuration adapted to permit the superior portion to be moved with respect to the inferior portion.

9. The orthopedic implant of claim 6 wherein the column further comprises a tab supported by the superior portion and biased by a spring, the spring biasing the tab into one of the connection slots to prevent relative movement between the superior portion and the inferior portion, the tab being movable against the spring out of the one of the connection slots to permit movement of the superior portion with respect to the inferior portion.

10. The orthopedic implant of claim 9 further comprising a button operatively connected to the tab to move the tab against the spring.

11. The orthopedic implant of claim 6 wherein the column further comprises a rotatable connection between the superior portion and the column, the rotatable connection having a first position permitting movement of the superior portion to a second connection position and a second position preventing movement of the superior portion from the first connection position to the second connection position.

\* \* \* \* \*